(12) United States Patent
Nakano

(10) Patent No.: US 9,113,806 B2
(45) Date of Patent: Aug. 25, 2015

(54) ENDOSCOPE APPARATUS FOR MEASURING A SPATIAL CHARACTERISTIC

(75) Inventor: Sumito Nakano, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 397 days.

(21) Appl. No.: 13/613,918

(22) Filed: Sep. 13, 2012

(65) Prior Publication Data

US 2013/0012776 A1  Jan. 10, 2013

Related U.S. Application Data

(62) Division of application No. 11/881,673, filed on Jul. 27, 2007, now Pat. No. 8,372,002.

(30) Foreign Application Priority Data

Jul. 27, 2006 (JP) .................. 2006-204818

(51) Int. Cl.
- A61B 1/00 (2006.01)
- A61B 1/04 (2006.01)
- A61B 1/05 (2006.01)
- A61B 5/107 (2006.01)
- G06T 7/00 (2006.01)

(52) U.S. Cl.
CPC .............. *A61B 1/05* (2013.01); *A61B 1/00009* (2013.01); *A61B 5/1076* (2013.01); *A61B 5/1079* (2013.01); *G06T 7/0075* (2013.01); *A61B 1/00193* (2013.01); *G06T 2207/10012* (2013.01); *G06T 2207/10068* (2013.01); *G06T 2207/30004* (2013.01)

(58) Field of Classification Search
CPC ........... A61B 1/00009; A61B 1/00193; A61B 5/1079; G06T 7/0075; G06T 2207/10012; G06T 2207/10068; G06T 2207/30004
USPC ................. 600/117, 118, 109, 111, 166, 921; 348/65, 74, 75, 135
See application file for complete search history.

(56) References Cited

U.S. PATENT DOCUMENTS

| 4,621,284 A | 11/1986 | Nishioka et al. |
| 5,668,631 A | 9/1997 | Norita et al. |
| 5,860,912 A | 1/1999 | Chiba |

(Continued)

FOREIGN PATENT DOCUMENTS

| JP | 2004-033487 A | 2/2004 |
| JP | 2004-049638 A | 2/2004 |

*Primary Examiner* — John P Leubecker
(74) *Attorney, Agent, or Firm* — Holtz, Holtz, Goodman & Chick PC

(57) ABSTRACT

An image converter receives image data of an object and performs a kind of image conversion on the image data to generate converted image data for display. A measurement section measures at least one spatial characteristic of the object based on: the converted image data, and optical data, which relates to optical characteristics of an optical system through which the image data of the object has been obtained, and which is made to correspond to the kind of image conversion performed by the image converter. Alternatively, a measurement section measures at least one spatial characteristic of the object by relating, based on the kind of image conversion, coordinates of the converted image data to coordinates of the image data of the object before the image conversion, and by measuring the at least one spatial characteristic based on the coordinates of the image data of the object before the image conversion.

10 Claims, 8 Drawing Sheets

(56) References Cited

U.S. PATENT DOCUMENTS

| | | |
|---|---|---|
| 6,063,023 A | 5/2000 | Sakiyama et al. |
| 6,120,435 A | 9/2000 | Eino |
| 6,339,446 B1 | 1/2002 | Miyoshi |
| 6,937,268 B2 | 8/2005 | Ogawa |
| 6,945,930 B2 | 9/2005 | Yokota |
| 7,170,677 B1 | 1/2007 | Bendall et al. |
| 7,520,854 B2 | 4/2009 | Sato |
| 2003/0060679 A1 | 3/2003 | Murata et al. |
| 2004/0030221 A1 | 2/2004 | Ogawa |
| 2004/0054256 A1 | 3/2004 | Ogawa |
| 2004/0225185 A1* | 11/2004 | Obata et al. .......... 600/118 |
| 2006/0161042 A1 | 7/2006 | Kobayashi et al. |
| 2006/0176321 A1* | 8/2006 | Nakano et al. ......... 345/660 |
| 2006/0178561 A1 | 8/2006 | Nakano et al. |
| 2006/0268257 A1* | 11/2006 | Ogawa .................. 356/3.13 |
| 2014/0184751 A1* | 7/2014 | Liou et al. ............... 348/47 |

* cited by examiner

ENDOSCOPE APPARATUS FOR MEASURING A SPATIAL CHARACTERISTIC

CROSS REFERENCE TO RELATED APPLICATION

This is a Divisional of U.S. application Ser. No. 11/881,673, filed Jul. 27, 2007, which issued as U.S. Pat. No. 8,372,002, and which is based upon and claims the benefit of priority from prior Japanese Patent Application No. 2006-204818, filed Jul. 27, 2006, the entire contents of both of which are incorporated herein by reference.

BACKGROUND OF THE INVENTION

1. Field of the Invention

This invention relates to an endoscope apparatus which can measure the spatial characteristics such as length, area, shape, and so on, of a photographic object.

2. Description of the Related Art

A stereo optical adapter through which images of an object of interest are taken is attached at a tip of an endoscope to form an endoscope apparatus which can measure various spatial characteristics of the object by the principle of triangulation (stereo measurement). Such an apparatus is widely used. (See, for example, JP 2004-33487A.) The stereo optical adapter may be, for example, a direct-view optical adapter or a side-view optical adapter.

FIG. 6 shows a side-view type stereo optical adapter attached to the tip portion of the endoscope. FIG. 7 is a cross-sectional view of the tip portion of the endoscope taken along line VII-VII of FIG. 6. As shown in FIGS. 6 and 7, a side-view stereo optical adapter 7 is attached to the tip portion 21 of the endoscope by a securing ring 50 by screwing a female screw 50a of the securing ring 50 on a male screw 21a of the endoscope tip portion 21. As shown in FIG. 6, a pair of optical lenses 56 and 57 and two objective lens systems 58 and 59 are formed in the tip portion of the side-view stereo optical adapter 7. As shown in FIG. 7, a prism 49a and an optical lens 49b which bend an optical axis 90 degrees are provided directly below the two objective lens systems 58 and 59. A view mask 55b which has two quadrilateral (for example) openings 55d (see FIG. 8) is arranged at the end face side (nearer to the tip portion 21 of the endoscope) of the optical lens 49b as shown in FIG. 7. On an imaging side of the solid-state image sensor 2a arranged in the endoscope tip portion 21, two optical images which have passed through the openings 55d of the view mask 55b are imaged to be observed as shown in FIG. 9. As shown in FIG. 9, when a photographic object 30 (object of interest), which is the character F in FIG. 6, is imaged, the side-view stereo optical adapter provides mirrored images 30aL and 30aR of the photographic object 30 due to the action of the prism 49b. Since the mirrored images may not be suitable for observation, the mirrored images of the photographic object may be horizontally inverted to be observed as erect images 30bL and 30bR, as shown in FIG. 10. Alternatively, a vertically inverted or rotated image may be suitable for observation depending on the action of the prism, and an enlarged or reduced image may be suitable depending on a size of the object of interest.

In order to perform stereo measurement by triangulation using the images obtained from two viewpoints as mentioned above, optical data including the optical characteristics of an optical system, such as the focal length of two or more optical systems, etc., is required. For this reason, the optical data has to be generated by measurement. See, for example, JP2004-49638A, the entire contents of which are incorporated herein by reference.

BRIEF SUMMARY OF THE INVENTION

According to one aspect of the present invention, an apparatus is provided which includes: an image converter which receives image data of an object and which performs a kind of image conversion on the image data to generate converted image data for display; and a measurement section which measures at least one spatial characteristic of the object based on: (i) the converted image data, and (ii) optical data, which relates to optical characteristics of an optical system through which the image data of the object has been obtained, and which is made to correspond to the kind of image conversion performed by the image converter.

According to another aspect of the present invention, a system is provided which includes: (i) an endoscope apparatus, which includes: an image sensor which images an object via an optical system and outputs image data of the object; and an image converter which receives the image data of the object and which performs a kind of image conversion on the image data to generate converted image data for display; and (ii) a processing apparatus, which includes: a measurement section which measures at least one spatial characteristic of the object based on: (i) the converted image data, which is obtained from the endoscope apparatus, and (ii) optical data, which relates to optical characteristics of the optical system through which the image data of the object has been obtained by the endoscope apparatus, and which is made to correspond to the kind of image conversion performed by the image converter of the endoscope apparatus. According to a further aspect of the present invention, an apparatus is provided which includes an image converter which receives image data of an object and which performs a kind of image conversion on the image data to generate converted image data for display; and a measurement section which measures at least one spatial characteristic of the object based on the image data by relating, based on the kind of image conversion, coordinates of the converted image data to coordinates of the image data of the object before the image conversion, and by measuring the at least one spatial characteristic based on the coordinates of the image data of the object before the image conversion.

BRIEF DESCRIPTION OF THE DRAWINGS

These and other features, and advantages of the apparatus and methods of the present invention will become better understood based on the following description, appended claims, and accompanying drawings wherein:

DETAILED DESCRIPTION OF THE EXAMPLES OF THE INVENTION

Embodiments of this invention, in which the invention is applied to an endoscope apparatus for measurement that is capable of performing stereo measurement, are described with reference to the drawings.

Figure 1:
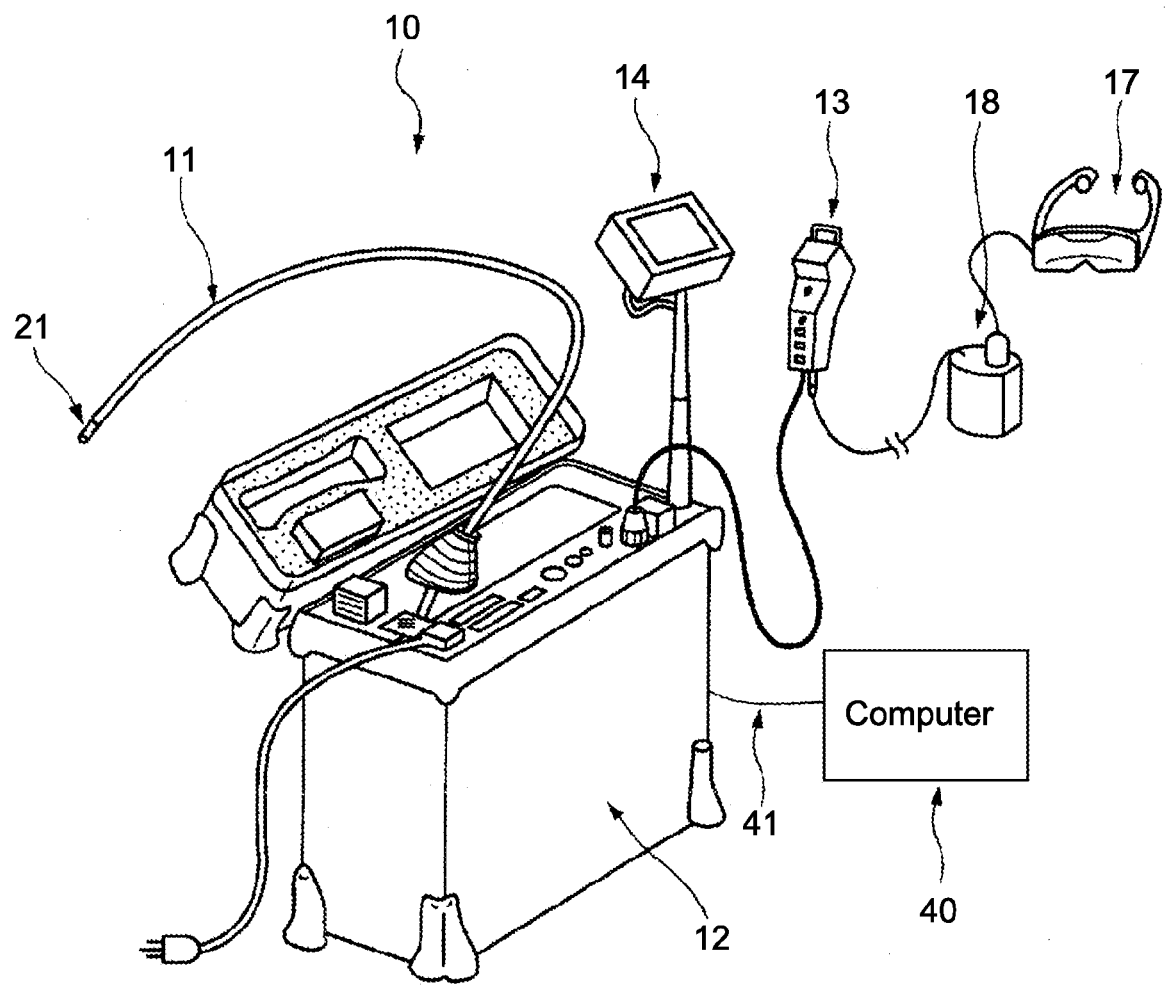
FIG. 1 is a diagram showing the structure of the endoscope apparatus for measurement according to one embodiment of this invention.

As shown in FIG. 1, the endoscope apparatus 10 for measurement includes an endoscope inserting portion 11, with the tip portion 21 at a tip (distal) end thereof, a control unit 12, a controller 13, a display 14, an FMD 17 (Face Mounted Display), and an FMD adapter 18. The control unit 12 includes a holding portion for storing the endoscope inserting portion 11. A computer 40 may be coupled to the endoscope apparatus 10 by a communication line 41, such as a USB line or a LAN, to enable communication between the computer 40 and the endoscope apparatus 10.

Figure 6:
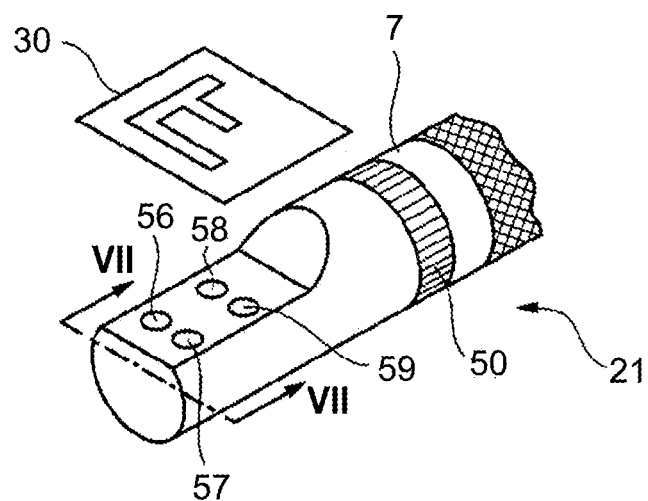
FIG. 6 is a perspective view of a tip portion of an endoscope with a side-view stereo optical adapter attached thereto.
Figure 7:
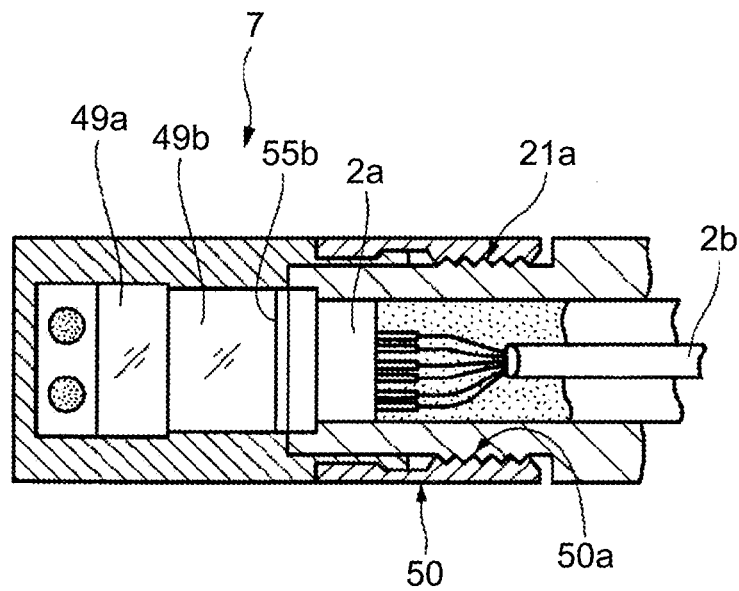
FIG. 7 is a sectional view along line VII-VII in FIG. 6.
Figure 8:
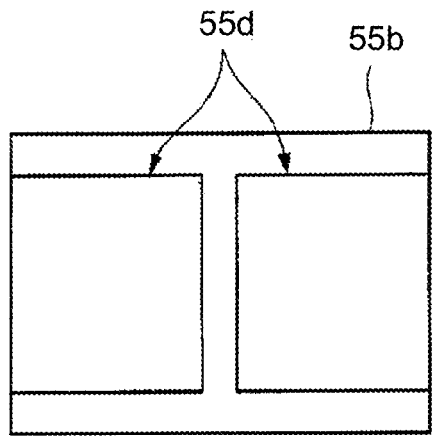
FIG. 8 is a reference drawing showing the view mask of the side-view stereo optical adapter.

A stereo optical adapter is attachable to and detachable from the tip portion 21 of the endoscope insertion portion 11 as shown in FIGS. 6 and 7 to collect light from an object of interest along two optical paths, so as to image the object using a solid-state image sensor 2a provided in the tip portion 21 (refer to FIGS. 2 and 7) from two view points (see FIGS. 8-10) to enable the endoscope apparatus to perform stereo measurement. The solid-state image sensor 2a converts optical signals of the object of interest which enter the sensor 2a via the optical adapter to electrical signals, and generates imaging signals. The control unit 12 processes the imaging signals outputted from the solid-state image sensor 2a.

The controller 13 is operable by a user to control various functions of the endoscope apparatus 10. The controller 13 transmits instructions input by the user to the control unit 12. The display 14, which is, for example, a LCD (Liquid Crystal Display) monitor, displays information such as an image (an endoscope image), graphics content for operating the endoscope apparatus 10 (for example, an operation menu), and so on. The graphics data may also be, for example, operating instructions, stereo measurement results, mode selection icons, and various other information. The FMD 17 displays a normal endoscope image or a pseudo corporal vision of the endoscope image as a stereo image. The FMD adapter 18 supplies the image data to the FMD 17.

Figure 2:
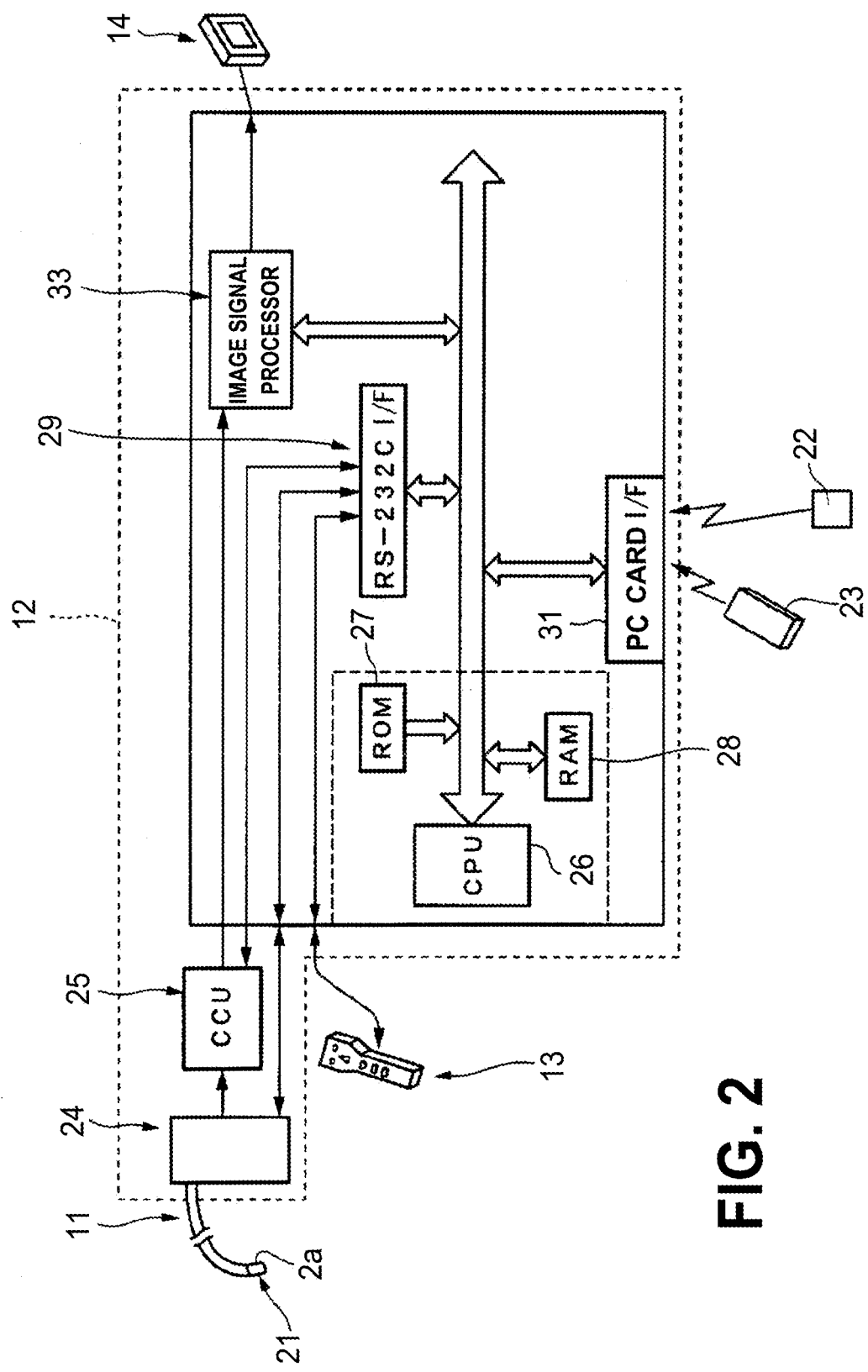
FIG. 2 is a block diagram showing the structure of the control unit with which the endoscope apparatus for measurement according to one embodiment of the invention is provided.

FIG. 2 shows the internal configuration of the control unit 12. As shown in FIG. 2, the endoscope inserting portion 11 is connected to the endoscope unit 24, which includes a light source for emitting illumination light required at the time of imaging, and an electrical bending device for electrically bending the endoscope inserting portion 11. The imaging signals from the solid-state image sensor 2a at the tip portion 21 of the endoscope inserting portion 11 are inputted into a CCU 25 (Camera Control Unit). The CCU 25 converts the supplied imaging signals into an image signal, such as an NTSC signal, and supplies the image signal to the main processing circuit group in the control unit 12.

As shown in FIG. 2, the main processing circuit group in the control unit 12 includes a CPU 26, a ROM 27, a RAM 28, a RS-232C I/F 29, a PC card I/F 31, and an image signal processor (i.e., processing circuit) 33. The CPU 26 executes a program stored in the ROM 27 and controls various circuits to control the endoscope apparatus 10. The RAM 28 is a workspace of various operations of the CPU 26. The RS-232C I/F 29 is connected to each of the controller 13, the endoscope unit 24 and the CCU 25. The controller 13 receives an operation input (operation instructions) from a user for controlling the endoscope unit 24 and the CCU 25. The RS-232C I/F 29 communicates with the controller 13 for controlling operation of the endoscope unit 24 and the CCU 25 based on the operation input from the controller 13. PC card I/F 31 is configured to enable flash memory card 22 and the PCMCIA memory card 23 to be attached and detached. That is, the control unit 12 loads control processing information, image information, optical data, etc. recorded on the memory card 22 or 23, for example, via the PC card I/F 31 according to control by CPU 26 when one of the memory cards is inserted in the PC card I/F 31. Furthermore, the control unit 12 can record data including control processing information, image information, optical data, etc., on the memory card 22 or 23 via the PC card I/F 31.

The CPU 26 generates graphics data corresponding to the graphics content, such as the operation menu, to be displayed on the display 14 and outputs the graphics data to the image signal processor 33. The image signal processor 33 creates a synthetic image by synthesizing image data corresponding to an endoscope image or images (e.g., left and right viewpoint images) supplied from the CCU 25 and the graphics data supplied from the CPU 26, and converts the synthesized data into an image signal, such as an NTSC signal, and supplies the image signal to the display 14. The display 14 displays the synthetic image of the endoscope image or images and the graphics content, such as the operation menu, based on the image signal. The image signal processor 33 can also perform processing to display only the endoscope image or images or only the graphics content, such as the operation menu, individually.

Figure 9:
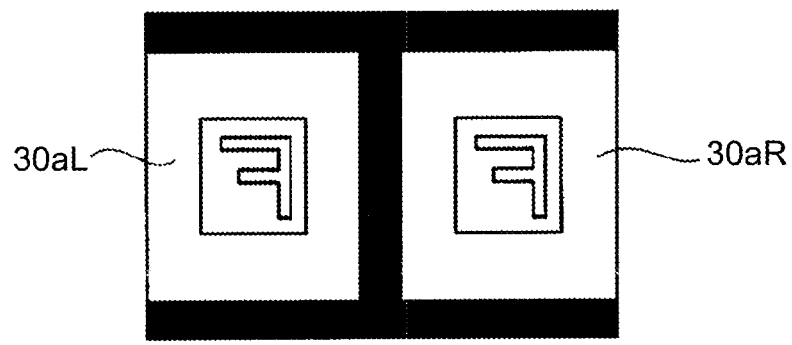
FIG. 9 is a reference drawing showing the image observed with the endoscope.
Figure 10:
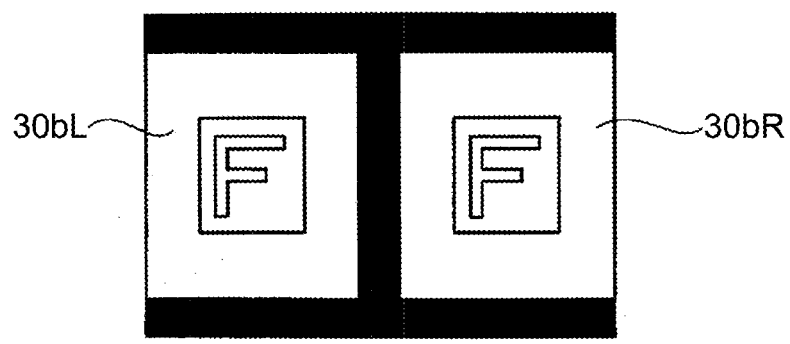
FIG. 10 is a reference drawing showing the image observed with the endoscope when the image is horizontally inverted.

Furthermore, the image signal processor 33 can perform an image conversion on the image data of the endoscope image, under the control of the CPU 26 based on the directions from the controller 13. The image conversion includes a horizontal inversion (also known as a horizontal flip or "flip horizontal" operation), a vertical inversion (also known as a vertical flip or "flip vertical" operation), a rotation by any angle, an expansion, and a reduction. For example, when mirrored endoscope images 30aL, 30aR shown in FIG. 9 are inverted horizontally, endoscope images 30bL, 30bR of FIG. 10 will be displayed on the screen of the display 14. Of course, the image signal processor is also capable of not performing an image conversion. When the type of image conversion is set as no conversion, the image signal processor 33 continues subsequent processes without performing the image conversion.

When processing the stereo measurement, the CPU 26 loads the endoscope image as image data from the image signal processor 33 and stores the endoscope image in the RAM 28, and also loads optical data from the recording medium (the flash memory card 22 or the PCMCIA memory card 23) into RAM 28, and the stereo measurement is performed based on the image data and the optical data.

Figure 3:
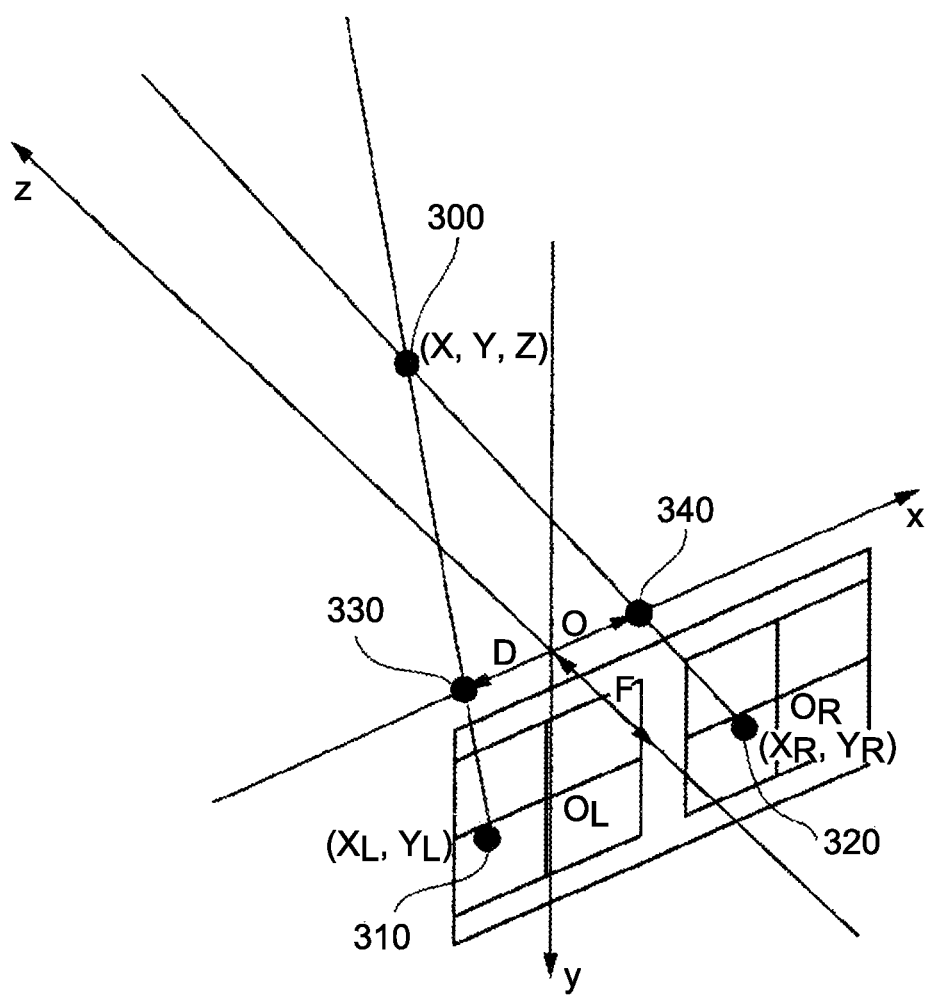
FIG. 3 is a reference drawing for explaining how to search for the three-dimensional coordinates of a measurement point by stereo measurement according to one embodiment of the invention.

According to this embodiment of the present invention, the light from the object is collected by the optical adapter along two right-and-left optical paths. Then image data for two images, corresponding respectively to the optical paths, are generated by the solid-state image sensor 2a and the CCU 25. That is, the image data for the two images correspond respectively to two viewpoints, namely a right viewpoint and a left viewpoint. The stereo measurement is performed based on these image data. Next, it is explained how to search for three-dimensional coordinates of a measurement point by stereo measurement with reference to FIG. 3.

First, the left and right viewpoint images are processed to correct geometric lens distortion so as to remove a geometric distortion resulting from the lens system through which the images were captured. Then, the three-dimensional coordinates (x, y, z) of a measurement point 300 on the object of interest is calculated by triangulation using the formulas:

$$x = t \times x_R + D/2$$

$$y = t \times y_R$$

$$z = t \times F$$

in which: $(x_L, y_L)$ are the coordinates of the measurement point 310, which is the position of the measurement point 300 in the image of the left viewpoint, which has been processed to correct the geometric lens distortion; $(x_R, y_R)$ are the coordinates of the measurement point 320, which is the position of the measurement point 300 in the image of the right viewpoint, which has been processed to correct the geometric lens distortion; D is a distance between the left optical center 330 and the right optical center 340; F is a focal length (see FIG. 3); and t is equal to $D/(x_L - x_R)$.

Accordingly, when the coordinates of measurement points 310, 320 are determined in the images of the left and right viewpoints after the processing to correct the geometric lens distortion, the three-dimensional coordinates of the measurement point 300 can be found using parameters D and F as mentioned above. The measurement points 310 and 320 may be entered by a user in each of the images of the left and right viewpoints. That is, the images of the left and right viewpoints, which have been processed to correct the geometric lens distortion, are displayed on, for example, the display 14. The user, by operating the controller 13, designates a point 310 in the left viewpoint image corresponding to a measurement point on the object of interest, and designates a point 320 in the right viewpoint image corresponding to the same point on the object of interest. The CPU 26 may also execute an automated matching process to automatically, for example, match a point 310 specified by the user in the left viewpoint image with a point 320 in the right viewpoint image, without requiring the user to manually specify the point 320 in the right viewpoint image.

The user may specify many measurement points 300 on the object of interest, by specifying a point 310 and a point 320 for each of the measurement points 300. By finding the three-dimensional coordinates of a number of measurement points 300, various spatial characteristics of the object of interest can be determined. For example, it is possible to measure: a distance to a single point (e.g., from an objective lens), a distance between two points, a distance between a line which connects two points and another point, an area, a depth, a surface shape, etc. This stereo measurement requires information regarding the optical characteristics of the optical system (in the optical adapter) and the endoscope tip portion 21, which is referred to herein as optical data. For example, the optical data can be measured by the method described in JP 2004-49638A. The measured optical data can be, for example, recorded on the recording medium (for example, the flash memory card 22 or the PCMCIA memory card 23).

The optical data includes: (a) a parameter of the correction of geometric distortion of each the right optical system and the left optical system in the optical adapter, (b) the focal length of each the right optical system and the left optical system, (c) the distance D between the optical centers of each of the right optical system and the left optical system, and (d) coordinates of the optical-axis positions (optical-axis positions $O_R$ and $O_L$ of FIG. 3) of each of the right and left optical systems on the right and left viewpoint images, respectively.

More specifically, with respect to correcting geometric distortion for the left viewpoint image, a distortion center is defined as $D_L = (D_{Lx}, D_{Ly})$, a position of a pixel before correction is defined as $P = (P_{Lx}, P_{Ly})$ and a position of the pixel after correction is defined as $P' = (P_{Lx}', P_{Ly}')$, where the position of the optical axis in the left viewpoint image is $O_L = (O_{Lx}, O_{Ly})$ and $O_L$ is the origin of $D_L$, P and P'. A distortion correction coefficient for the left viewpoint image is $A_L = (A_{L1}, A_{L2})$, $B_L = (B_{L1}, B_{L2})$ and the geometric distortion is corrected by the following formulas:

$$P_{Lx}' = A_{L1}(P_{Lx} - D_{Lx})^3 + A_{L2}(P_{Lx} - D_{Lx})(P_{Ly} - D_{Ly})^2 + D_{Lx} + P_{Lx}$$

$$P_{Ly}' = B_{L1}(P_{Lx} - D_{Lx})^2(P_{Ly} - D_{Ly}) + B_{L2}(P_{Ly} - D_{Ly})^3 + D_{Ly} + P_{Ly}$$

Similarly, with respect to correcting geometric distortion for the right viewpoint image, a distortion center is defined as $D_R = (D_{Rx}, D_{Ry})$, a position of a pixel before correction is defined as $P = (P_{Rx}, P_{Ry})$ and a position of the pixel after correction is defined as $P' = (P_{Rx}', P_{Ry}')$, where the position of the optical axis in the right viewpoint image is $O_R = (O_{Rx}, O_{Ry})$ and $O_R$ is the origin of $D_R$, P and P'. A distortion correction coefficient for the right viewpoint image is $A_R = (A_{R1}, A_{R2})$, $B_R = (B_{R1}, B_{R2})$, and the geometric distortion is corrected by the following formulas:

$$P_{Rx}' = A_{R1}(P_{Rx} - D_{Rx})^3 + A_{R2}(P_{Rx} - D_{Rx})(P_{Ry} - D_{Ry})^2 + D_{Rx} + P_{Rx}$$

$$P_{Ry}' = B_{R1}(P_{Rx} - D_{Rx})^2(P_{Ry} - D_{Ry}) + B_{R2}(P_{Ry} - D_{Ry})^3 + D_{Ry} + P_{Ry}$$

Moreover, in the optical data the focal length of the right optical system is $F_R$ and the focal length of the left optical system is $F_L$. The distance D between the optical centers of each right and left optical systems is given by a vector from the right optical system to the left optical system $V_{LR} = (V_{LRx}, V_{LRy}, V_{LRz})$. And as noted above, the position of the optical axis on the image of the left viewpoint is $O_L = (O_{Lx}, O_{Ly})$, and the position of the optical axis on the image of the right viewpoint is $O_R = (O_{Rx}, O_{Ry})$.

This optical data is initially obtained by a manufacturer of an optical adapter and stored in a recording medium (e.g., memory card 22 or 23) by the manufacturer. This optical data is, for example, obtained by the manufacturer by coupling the optical adapter to a master endoscope and then measuring the optical data. When an end-user first uses the optical adapter, the data obtained by the manufacturer that is stored on the memory card 22 or 23, for example, is modified during a setup process based on the relationship between the optical adapter and the particular endoscope used by the end-user. In particular, the data concerning the parameter of the correction of geometric distortion of each the right optical system and the left optical system in the optical adapter, and the coordinates of the optical-axis positions (optical-axis positions $O_R$ and $O_L$ of FIG. 3) of each of the right and left optical systems on the right and left viewpoint images, respectively, is modified during a setup process to correspond to the specific combination of the optical adapter and the endoscope with which the optical adapter will be used. The converted optical data, which has been converted to be specific to the combination of the optical adapter and the endoscope of the end user, is referred to herein as "initial" or "original" optical data. The initial optical data is stored on the recording medium, such as the memory card 22 or 23, for example. (The optical data specific to the combination of the optical adapter and the endoscope may sometimes be referred to as "environment data" in the art, while the optical data generated by the manufacturer is sometimes referred to as "optical data" in the art. These terms should not be confused with the terms used in the present application.) The optical data are measured by the manufacturer in a state in which the image conversion is set to a predetermined condition (for example, no conversion). Thus, the "initial" or "original" optical data relates to the predetermined condition. Since the characteristics of the parameter of the correction, the focal length and the optical-axis positions on the images, etc., change when a different image conversion from the predetermined condition is performed, it becomes impossible to use the original optical data for a measurement when a different image conversion is performed. Thus, in this embodiment of the present invention, new optical data corresponding to another image conversion are generated by converting the measured original optical data.

Figure 4:
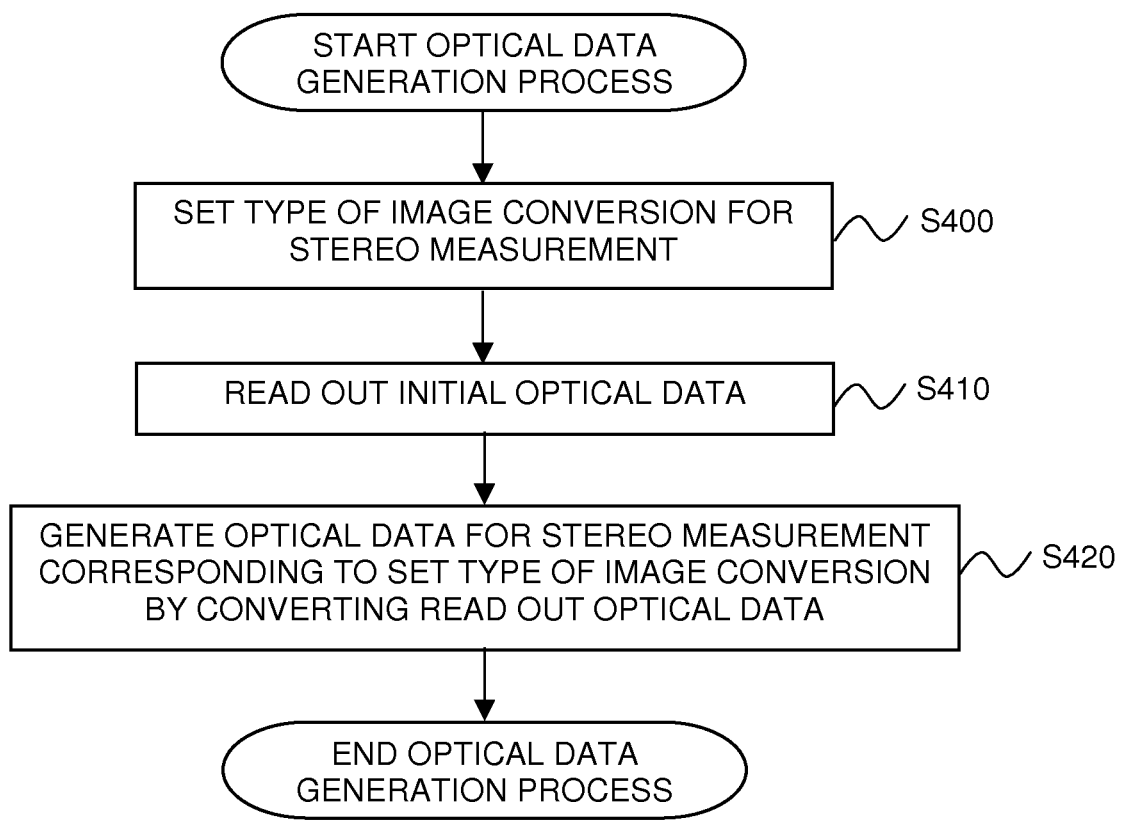
FIG. 4 is a flowchart which shows the procedure for generating optical data for stereo measurement according to one embodiment of the invention.

With reference to FIG. 4, the method of generating the optical data in this embodiment is explained. First, the CPU 26 sets a type of image conversion for stereo measurement (for example, at least one of the horizontal inversion, the vertical inversion, the rotation, the expansion, and the reduction) based on a signal outputted from the controller 13 (Step S400). Then, the CPU 26 reads out the initial optical data from the recording medium and sets the initial optical data (Step S410). The information concerning these settings is stored in the RAM 28, for example, and referred to suitably by the CPU 26.

Then, the CPU 26 generates the optical data for stereo measurement by converting the read out initial optical data for stereo measurement in accordance with the kind of image conversion for stereo measurement (Step S420), and writes the optical data for stereo measurement in the recording medium (e.g., flash memory card 22 or the PCMCIA memory card 23).

The process shown in FIG. 4 may be performed for each of the kinds of image conversion (for example, horizontal inversion, vertical inversion, rotation and expansion and reduction), or for a plurality of kinds of image conversion that are applicable to a given optical adapter, and converted optical data corresponding to each kind of image conversion for stereo measurement may be stored on the recording medium. Each optical data is recorded on the recording medium such that it is related with the identification information on the type of the image conversion.

In addition, a plurality of optical adapters may be used with the endoscope apparatus, and the process of obtaining the initial optical data via the setup process described above, and the process shown in FIG. 4 to generate optical data for stereo measurement, for the various kinds of image conversion may be performed for each optical adapter.

In more detail, the conversion of the optical data (Step S420) is performed as follows. The conversion of the optical data is explained below using the condition that the image conversion for optical data measurement is "no conversion" as an example. When the image conversion for stereo measurement is the horizontal inversion, each of the left and right viewpoint images are inverted horizontally, and the optical systems are switched. The optical data is converted as follows ("prime" indicates the optical data after conversion).

$D_L' = (-D_{Rx}, D_{Ry})$;

$D_R' = (-D_{Lx}, D_{Ly})$;

$A_L' = (A_{R1}, A_{R2})$;

$B_L' = (B_{R1}, B_{R2})$;

$A_R' = (A_{L1}, A_{L2})$;

$B_R' = (B_{L1}, B_{L2})$;

$F_R' = F_L$;

$F_L' = F_R$;

$V_{LR}' = (V_{LRx}, -V_{LRy}, -V_{LRz})$;

$O_L' = (a-(O_{Rx}-a), O_{Ry})$; and $O_R' = (a+(a-O_{Lx}), O_{Ly})$, where $a$ is the x-coordinate of the axis about which the inversion is performed.

When the image conversion for stereo measurement is the vertical inversion, each of the left viewpoint image and the right viewpoint image is inverted vertically. The optical data is converted as follows ("prime" indicates the optical data after conversion).

$D_L' = (D_{Lx}, -D_{Ly})$;

$D_R' = (D_{Rx}, -D_{Ry})$;

$A_L' = A_L$ (unchanged);

$B_L' = B_L$ (unchanged);

$A_R' = A_R$ (unchanged);

$B_R' = B_R$ (unchanged);

$F_R' = F_R$ (unchanged);

$F_L' = F_L$ (unchanged);

$V_{LR}' = (V_{LRx}, -V_{LRy}, V_{LRz})$;

$O_L' = (O_{Lx}, b-(O_{Ly}-b))$; and $O_R' = (O_{Rx}, b-(O_{Ry}-b))$, where $b$ is the y-coordinate of the axis about which the inversion is performed.

When the image conversion for stereo measurement is the rotation, the parameters of the correction of geometric distortion and the optical-axis position coordinates on the images are rotated. For example, when the rotation is to the left, for each of the original left and right viewpoint images, each point (x, y) of the original image is converted to (y, w-x), where w is the width of the original image. The optical data is converted as follows ("prime" indicates the optical data after conversion).

$D_L' = (D_{Ly}, D_{Lx})$;

$D_R' = (D_{Ry}, D_{Rx})$;

$A_L' = (B_{L2}, B_{L1})$;

$B_L' = (A_{L2}, A_{L1})$;

$A_R' = (B_{R2}, B_{R1})$;

$B_R'=(A_{R2},A_{R1})$;

$F_R'=F_R$ (unchanged);

$F_L'=F_L$ (unchanged);

$V_{LR}'=(-V_{LRy},V_{LRx},V_{LRz})$;

$O_L'=(O_{Ly},w-O_{Lx})$; and $O_R'=(O_{Ry},w-O_{Rx})$.

When the image conversion for stereo measurement is the expansion/reduction, the parameters of the correction of geometric distortion, the focal length, the distance between the optical centers, and the optical-axis position coordinates on the images are expanded/reduced according to the expansion/reduction rate. More specifically, when the image conversion for stereo measurement is expansion or reduction, for each of the original left and right viewpoint images, each point (x, y) in the original image is converted to (m(x−w/2)+x, m(y−h/2)+y), where w and h are the width and height, respectively, of the original image, and m is the magnifying or reducing power. When m is greater than 1, the image is magnified. When m is smaller than 1, the image is reduced. The optical data is converted as follows ("prime" indicates the optical data after conversion).

$D_L'=(m(D_{Lx}-w/2)+D_{Lx},m(D_{Ly}-h/2)+D_{Ly})$;

$D_R'=(m(D_{Rx}-w/2)+D_{Rx},m(D_{Ry}-h/2)+D_{Ry})$;

$A_L'=(A_{L1}/m^3,A_{L2}/m^3)$;

$B_L'=(B_{L1}/m^3,B_{L2}/m^3)$;

$A_R'=(A_{R1}/m^3,A_{R2}/m^3)$;

$B_R'=(B_{R1}/m^3,B_{R2}/m^3)$;

$F_R'=mF_R$;

$F_L'=mF_L$;

$V_{LR}'=(V_{LRx},V_{LRy},V_{LRz})$ (unchanged);

$O_L'=(m(O_{Lx}-w/2)+O_{Lx},m(O_{Ly}-h/2)+O_{Ly})$; and $O_R'=(m(O_{Rx}-w/2)+O_{Rx},m(O_{Ry}-h/2)+O_{Ry})$.

As explained above, the manufacturer initially obtains optical data corresponding to an optical adapter, and the optical data is converted to the initial optical data for use with the endoscope of the end user in a setup process. The manufacturer may generate optical data corresponding to a kind of image conversion that is preferred or required for use with the optical adapter. This kind of image conversion may, for example, be associated with the optical adapter as a default kind of image conversion. For example, when a side-view optical adapter that requires image data to be vertically inverted for display, for example, is manufactured, the manufacturer may generate optical data corresponding to the vertical inversion.

Figure 5:
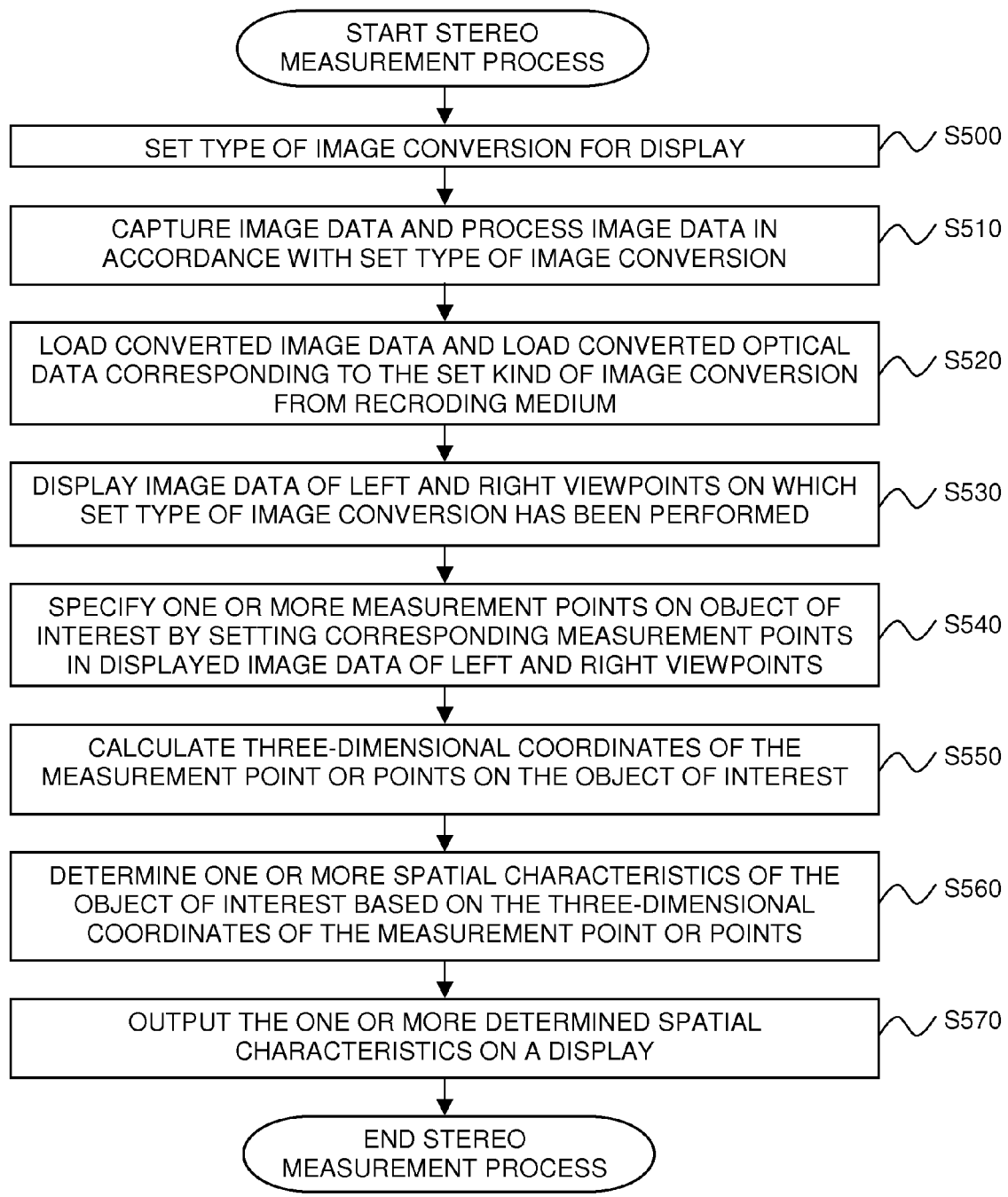
FIG. 5 is a flowchart which shows the processing procedure at the time of the stereo measurement according to one embodiment of the invention.

Next, with reference to FIG. 5, the processing at the time of stereo measurement is explained. A kind of image conversion to be performed for display is set (Step S500). The user, using controller 13, may set the kind of image conversion to be performed for display. The CPU 26 sets kind of the image conversion for stereo measurement to the image signal processor 33. The kind of image conversion for display (corresponding to the kind of image conversion for stereo measurement) can alternatively be set automatically by the endoscope apparatus. For example, as explained above, a certain type of image conversion may be required (or preferred) for display when using a particular optical adapter. When an optical adapter is attached to the tip portion 21 of the endoscope, the CPU 26 of the endoscope apparatus may recognize the optical adapter and a type of image conversion required or preferred for the optical adapter based on a unique resistance, an IC chip, or so on, of the optical adapter. Alternatively, the user may select (e.g., via the controller 13) the optical adapter being used from a menu/list of optical adapters for use with the endoscope apparatus, and since a particular type of image conversion may be required or preferred for the optical adapter, the CPU 26 may set the kind of image conversion for display/stereo measurement to the kind of image conversion required for the optical adapter. Although not required in this embodiment, the manufacturer may provide information relating to the kind of image conversion required (or preferred) for the optical adapter on the memory card 22 or 23, for example, and it is also possible for a user to preliminarily associate (via data stored on the memory card or in another recording medium of the endoscope apparatus, for example) a specific kind of image conversion with the optical adapter. The user may also select (e.g., using the controller 13) the type of image conversion that is needed to display the image properly (for example, if the object of interest is hard to see). For example, the user may select rotation of the image data, and/or input a degree of expansion or reduction of the image as a type of image conversion (of course, the user may also select other kinds of image conversions). When the type of image conversion is automatically selected based on the recognition or selection of the optical adapter, the user may select further one or more image conversions to be performed. When the type of image conversion is not automatically determined, the user may manually input one or more image conversions.

The image data is captured via the solid-state image sensor and CCU 25 as explained above, and the image signal processor corrects the geometric distortion and performs the set kind of image conversion (Step S510). The CPU 26 loads the converted image data from the image signal processor 33 and stores the image data in the RAM 28, and the CPU 26 loads the converted optical data corresponding to the set kind of the image conversion from the recording medium, and stores the optical data in the RAM 28 (Step S520). The converted left and right viewpoint images are displayed (for example, on the display 14) with graphics content as explained above (Step S530), and a user specifies a measurement point or points 300 on the object of interest by setting the measurement points 310 and 320 in the left and right viewpoint images, as explained above (Step S540). The CPU 26 calculates the three-dimensional coordinates of the measurement point or points by triangulation, as explained above, based on the converted image data and the converted optical data (Step S550). Using the three-dimensional coordinates of the measurement point or points, the CPU 26 determines one or more spatial characteristics of the object of interest, such as a distance between two points, a distance between a line which connects two points and another point, an area, a depth, a surface shape, etc (step S560). Information (e.g., numerical values) representing the spatial characteristic(s) are output to a user on, for example, the display 14 (step S570).

It is also possible according to the present invention to measure and store only the initial optical data which becomes the origin of conversion. Then, when processing stereo measurement, the CPU 26 converts the initial optical data, which is, for example, read from the memory card 22 or 23, into optical data for stereo measurement in accordance with the set kind of image conversion before the stereo measurement is performed. When it is known before stereo measurement that two or more optical data are required (for example, if the user knows that a rotation of the image data must be performed in addition to or after an expansion of the image data), the optical data corresponding to the kinds of image conversion to be performed are obtained before the stereo measurement. Thus, the optical data corresponding to the predetermined image conversion (the optical data that is the origin in the conversion processing) may be stored beforehand in the memory card 22 or 23, and it may be converted to the optical data corresponding to the image conversion for stereo measurement before the stereo measurement is performed.

With this modification, the optical data for stereo measurement can be stored on the memory card and then erased from the recording medium after performing the stereo measurement, use, or need not be stored on the memory card at all thereby allowing an the amount of data stored on a recording medium to be minimized.

As explained above, according to this embodiment, the optical data used for measurement of the object's spatial characteristics is obtained by converting the initial optical data which is the origin of conversion according to the kind of the image conversion for stereo measurement. Accordingly, it is unnecessary to measure new optical data for the various kinds of image conversion. That is, only the initial optical data which serves as the origin of conversion is measured (i.e., measured by the manufacturer and processed in a setup process by the user), while the optical data corresponding to other kinds of image conversion (in the example above, all kinds of image conversion except "no conversion") are generated based on the measured initial optical data, whereby the time and effort required for measurement of an object's spatial characteristics can be reduced.

In the embodiment described above, the CPU 26 of the control unit 12 of the endoscope apparatus 10 loads the converted image data from the image signal processor 33 and loads from the recording medium such as the memory card 22 or 23 (or generates) the optical data corresponding to the kind of image conversion, and the CPU 26 calculates the three-dimensional coordinates of the measurement point(s) by triangulation. In addition, in the embodiment described above, the CPU 26 determines one or more spatial characteristics of the object of interest using the three-dimensional coordinates of the measurement point or points. According to the modification described above, the CPU 26 may load the initial optical data and generate the optical data corresponding to the kind of image conversion after the types of image conversion for the stereo measurement are set at the time of stereo measurement (but, of course, before measurement processing relying on the converted optical data is executed).

However, the CPU 26 need not perform all of these functions according to the present invention. Instead, the converted image data, which has been converted by the image signal processor 33, and the converted optical data (either read from the recording medium or generated by the CPU 26) may be transmitted to the computer 40 via the communication line 41. The computer 40 may then calculate the three-dimensional coordinates of the measurement point(s) by triangulation, and the computer 40 may then determine one or more spatial characteristics of the object of interest using the three-dimensional coordinates of the measurement point or points. In other words, the computer 40, instead of the CPU 26, may serve as a measurement section to measure one or more spatial characteristics of the object of interest. In addition, the computer 40 may obtain the initial optical data and may perform the conversion of the optical data to the optical data corresponding to the set kind of image conversion for stereo measurement. Thus, the computer 40 may receive the converted image data, information specifying the kind of conversion, and the initial optical data, and may measure one or more spatial characteristics of the object of interest using the received data.

According to the embodiments described above, the CPU 26 or the computer 40 calculates the three-dimensional coordinates of the measurement point(s) by triangulation using the image data that has been subjected to image conversion by the image signal processor 33 and using the converted optical data that has been converted in accordance with the set kind of image conversion. However, the three-dimensional coordinates of the measurement point(s) need not be measured using the converted image data and the converted optical data. Instead, the three-dimensional coordinates of the measurement point(s) can be measured using the image data that has not been subjected to the image conversion, and using the original or initial measured optical data.

Figure 11:
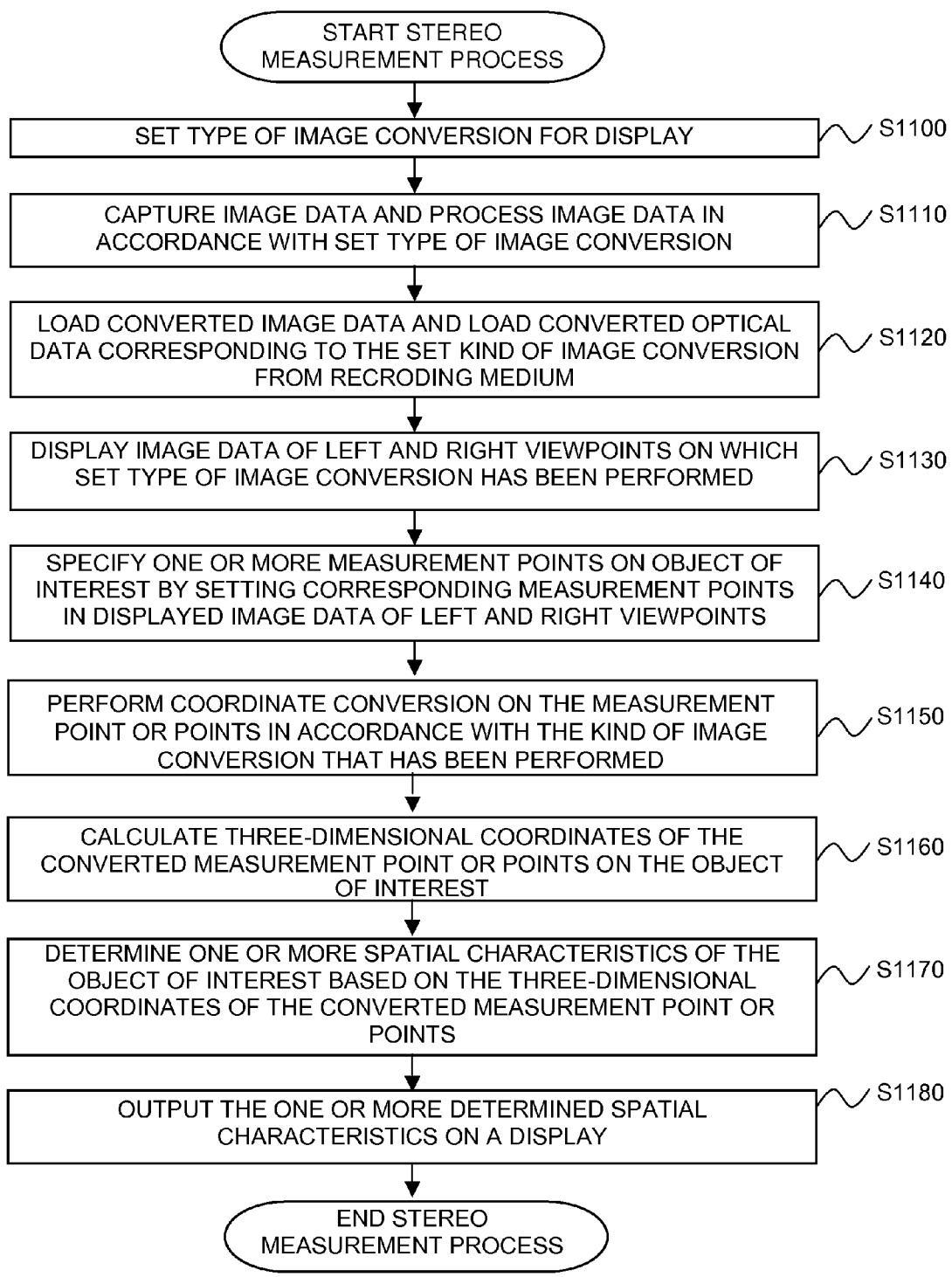
FIG. 11 is a flowchart which shows the processing procedure at the time of the stereo measurement according to another embodiment of the invention.

As shown in FIG. 11, according to this embodiment, in the same manner as the embodiments described above the user, using controller 13, sets a kind of image conversion to be performed for display (Step S1100). The CPU 26 sets kind of the image conversion for stereo measurement to the image signal processor 33. The image data is captured via the solid-state image sensor and CCU 25 as explained above, and the image signal processor 33 corrects the geometric distortion and performs the set kind of image conversion (Step S1110). The CPU 26 loads the converted image data from the image signal processor 33 and stores the image data in the RAM 28, and the CPU 26 loads the converted optical data corresponding to the set kind of the image conversion from the recording medium, and stores the optical data in the RAM 28 (Step S1120). The converted left and right viewpoint images are displayed (for example, on the display 14) with graphics content as explained above (Step S1130), and a user specifies a measurement point or points 300 on the object of interest by setting the measurement points 310 and 320 in the left and right viewpoint images for each measurement point 300, as explained above (Step S1140).

Then, in contrast to the embodiments described above, the CPU 26 performs a coordinate conversion on the measurement points 310 and 320 in accordance with the kind of image conversion that has been performed in order to convert the coordinates of the points 310 and 320 in the converted image data into coordinates in the image data before the conversion has been performed (but after the image data has been processed to correct the geometric distortion) (Step S1150). Using the converted coordinates of the points 310 and 320 and the initial (measured) optical data, which the CPU 26 loads from the recording medium (memory card 22 or 23 or ROM 27, for example), the CPU 26 calculates the coordinates of each measurement point 300 by triangulation (Step S1160) using the formulas:

$$X = t \times x_R' + D/2$$

$$y = t \times y_R'$$

$$z = t \times F$$

in which: $(x_L', y_L')$ are the coordinates of the measurement point 310 corresponding to the measurement point 300 in the image of the left viewpoint, and which have been converted to correspond to coordinates in the image data before the image conversion which has been processed to correct the geometric lens distortion; $(x_R', y_R')$ are the coordinates of the measurement point 320 corresponding to the measurement point 300 in the image of the right viewpoint, and which have been converted to correspond to coordinates in the image data before the image conversion which has been processed to correct the geometric lens distortion; D is a distance between the left optical center 330 and the right optical center 340; F is a focal length (see FIG. 3); and t is equal to $D/(x_L'-x_R')$.

Using the three-dimensional coordinates of the measurement point or points, the CPU 26 determines one or more spatial characteristics of the object of interest, such as a distance between two points, a distance between a line which connects two points and another point, an area, a depth, a surface shape, etc (Step S1170). Information (e.g., numerical values) representing the spatial characteristic(s) are output to a user on, for example, the display 14 (step S1180).

In the foregoing embodiments, the determined one or more spatial characteristics of the object of interest may be outputted to the user by displaying values corresponding to the one or more spatial characteristics (e.g., a distance value, area value, etc.) on the display 14 and/or the face mounted display 17. The CPU 26 may also, for example, cause the spatial characteristic(s) to be recorded in a recording medium, which may be internal to or removable from the endoscope apparatus. The determined spatial characteristic(s) may also, for example, be output to the computer 40 for display, printing or recording on a recording medium. When the computer 40 determines the spatial characteristic(s), the computer 40 may, for example, output the spatial characteristic(s) by display, printing or recording on a recording medium. Of course, other techniques of outputting the spatial characteristic(s) according to the present invention may be used, to provide the determined spatial characteristic(s) to the user and/or to another apparatus.

It will be obvious to those having skill in the art that many changes may be made in the above-described details of the preferred embodiments of the present invention. For example, although the foregoing embodiments have been described in connection with an endoscope apparatus, other image-capturing apparatuses may be used in connection with the techniques and structure described hereinabove. The scope of the present invention, therefore, should be determined by the following claims.

What is claimed is:

1. An apparatus comprising:
an image converter which receives image data of an object and which performs a kind of image conversion on the image data to generate converted image data for display; and
a measurement section which determines coordinates of the converted image data and measures at least one spatial characteristic of the object based on the image data by relating, based on the kind of image conversion, the coordinates of the converted image data to coordinates of the image data of the object before the image conversion, and by measuring the at least one spatial characteristic based on the coordinates of the image data of the object before the image conversion.

2. The apparatus according to claim 1, further comprising an image sensor which images the object via an optical system and outputs the image data to the image converter.

3. The apparatus according to claim 2, wherein the imaging sensor images the object from two viewpoints, and generates respective image data corresponding to each of the viewpoints, and the image converter performs the set image conversion on the image data of the two viewpoints; and wherein the measurement section measures the spatial characteristic of the object by triangulation using the respective image data of the two viewpoints.

4. The apparatus according to claim 3, wherein the measurement section performs the measurement with respect to at least one measurement point of the object;
wherein each said measurement point of the object corresponds to: a first measurement point having coordinates specified in the converted image data of a first one of the two viewpoints, and a second measurement point having coordinates specified in the converted image data of a second one of the two viewpoints;
wherein the measurement section converts: the specified coordinates of the first measurement point of each said measurement point of the object into coordinates in the image data of the first viewpoint before the image conversion, and the specified coordinates of the second measurement point of each said measurement point of the object into coordinates in the image data of the second viewpoint before the image conversion; and
wherein the measurement section performs the measurement for each said measurement point of the object using the converted coordinates of the first and second measurement points corresponding to the measurement point of the object.

5. The apparatus according to claim 4, further comprising:
a display which displays the converted image data of each of the two viewpoints; and
an input section operable by a user to specify each measurement point of the object by specifying the first measurement point in the converted image data of the first viewpoint and specifying the second measurement point in the converted image data of the second viewpoint.

6. The apparatus according to claim 1, wherein the measurement section performs the measurement with respect to at least one measurement point of the object;
wherein the at least one measurement point has coordinates specified in the converted image data, and the measurement section converts the specified coordinates of the at least one measurement point into coordinates in the image data of the object before the image conversion; and
wherein the measurement section performs the measurement using the converted coordinates of the measurement point in the image data before the image conversion.

7. The apparatus according to claim 6, further comprising:
a display which displays the converted image data; and
an input section operable by a user to specify the at least one measurement point in the displayed converted image data.

8. The apparatus according to claim 1, wherein the image data received and converted by the image converter comprises image data of the object from two viewpoints, and the measurement section measures the spatial characteristic of the object by triangulation using the respective image data of the two viewpoints.

9. The apparatus according to claim 8, wherein the measurement section performs the measurement with respect to at least one measurement point of the object;
wherein each said measurement point of the object corresponds to: a first measurement point having coordinates specified in the converted image data of a first one of the two viewpoints, and a second measurement point having coordinates specified in the converted image data of a second one of the two viewpoints;

wherein the measurement section converts the specified coordinates of the first measurement point of each said measurement point of the object into coordinates in the image data of the first viewpoint before the image conversion, and the specified coordinates of the second measurement point of each said measurement point of the object into coordinates in the image data of the second viewpoint before the image conversion; and wherein the measurement section performs the measurement for each said measurement point of the object using the converted coordinates of the first and second measurement points corresponding to the measurement point of the object.

10. The apparatus according to claim 9, further comprising:

a display which displays the converted image data of each of the two viewpoints; and an input section operable by a user to specify each measurement point of the object by specifying the first measurement point in the converted image data of the first viewpoint and specifying the second measurement point in the converted image data of the second viewpoint.

* * * * *